US009280641B2

(12) United States Patent
Collins et al.

(10) Patent No.: US 9,280,641 B2
(45) Date of Patent: Mar. 8, 2016

(54) MECHANISM FOR REMOTELY FACILITATING AUTHORIZATION AND ACTIVATION OF LABORATORY PRINT MEDIA LABELING

(75) Inventors: Mark Andrew Collins, Dripping Springs, TX (US); Charles W. Morrison, Jarrell, TX (US)

(73) Assignee: VAPORPRINT, LLC, Morrison, CO (US)

( * ) Notice: Subject to any disclaimer, the term of this patent is extended or adjusted under 35 U.S.C. 154(b) by 582 days.

(21) Appl. No.: 13/092,749

(22) Filed: Apr. 22, 2011

(65) Prior Publication Data

US 2012/0268773 A1    Oct. 25, 2012

(51) Int. Cl.
G06F 19/00    (2011.01)
G06F 3/12    (2006.01)
B41J 3/407    (2006.01)

(52) U.S. Cl.
CPC ............... *G06F 19/366* (2013.01); *B41J 3/407* (2013.01); *G06F 3/1204* (2013.01); *G06F 3/1205* (2013.01); *G06F 3/1253* (2013.01); *G06F 3/1268* (2013.01); *G06F 3/1285* (2013.01)

(58) Field of Classification Search
None
See application file for complete search history.

(56) References Cited

U.S. PATENT DOCUMENTS

| 5,662,821 | A * | 9/1997 | Ruckl | 219/121.67 |
| 6,452,692 | B1 * | 9/2002 | Yacoub | 358/1.15 |
| 2003/0120633 | A1 | 6/2003 | Torre-Bueno | |
| 2003/0231328 | A1 * | 12/2003 | Chapin et al. | 358/1.13 |
| 2004/0098165 | A1 * | 5/2004 | Butikofer | 700/235 |
| 2004/0184058 | A1 * | 9/2004 | Miyajima | 358/1.12 |
| 2005/0243161 | A1 * | 11/2005 | Wong | B41J 2/45 347/238 |
| 2007/0098900 | A1 | 5/2007 | Abe et al. | |
| 2007/0141711 | A1 * | 6/2007 | Stephens et al. | 436/43 |
| 2008/0056951 | A1 | 3/2008 | Angros | |
| 2008/0235055 | A1 | 9/2008 | Mattingly | |
| 2009/0003151 | A1 | 1/2009 | Honda et al. | |
| 2009/0210254 | A1 | 8/2009 | Gurney | |
| 2009/0303522 | A1 * | 12/2009 | Konsella | 358/1.15 |

* cited by examiner

*Primary Examiner* — Ming Hon
(74) *Attorney, Agent, or Firm* — Blakely Sokoloff Taylor & Zafman LLP (57) ABSTRACT

A method for remotely facilitating labeling of laboratory media may include placing a user request at a computing system serving as a remote computing system, the user request including print content to remotely facilitate labeling of a laboratory media within a laboratory environment. The laboratory media may include at least one of a media cassette or a media slide to hold one or more laboratory samples. The method may further include communicating the user request from the computing system to a printing device over a network. The printing device representing a local computing system. The method may further include remotely facilitating the printing device to label the laboratory media.

15 Claims, 5 Drawing Sheets

MECHANISM FOR REMOTELY FACILITATING AUTHORIZATION AND ACTIVATION OF LABORATORY PRINT MEDIA LABELING

RELATED APPLICATIONS

The present application is related to co-filed U.S. patent application Ser. No. 13/092687 entitled "Mechanism for Labeling Laboratory Print Media" and U.S. patent application Ser. No. 13/092728 entitled "Mechanism for Coating Laboratory Media with Photo-Sensitive Material", which are assigned to the assignee of the present application.

TECHNICAL FIELD

The embodiments of the invention relate generally to media printing and, more specifically, relate to providing a mechanism for remotely facilitating authorization and activation of laboratory print media labeling.

BACKGROUND

Good Laboratory Practices (GLP) standards dictate that medical or laboratory samples (e.g., histologic specimen, such as microscopic anatomy of cells and tissues of plants, animals, and humans) are to be identified and their medical containers (herein referred to as "print media", "media", "laboratory media", "media containers", or "media supplies") (e.g., slides, cassettes, test tubes, flasks, etc.) be labeled as soon as a sample enters a medical laboratory in order to identify and track the sample and to reduce any potential errors caused by improper identification of the sample. To address these concerns, special laboratory printers (herein referred to as "printing devices" or simply as "printers") were developed. Laboratory printers are commonly used to print laboratory print media with certain identifying information. Typically, once a print media has been printed with a label, the sample contained on or within the media can be tracked throughout the process within the laboratory. However, due to various laboratory printer-related problems (such as high cost of the printer, and other technology- and non-technology-related limitations), many laboratories offer high cost of printing or, in many cases, are forced to employ hand- or manual-labeling of the media.

To further enhance laboratory efficiency, software applications and systems (e.g., Laboratory Information System (LIS), Laboratory Integration Management Solution or Laboratory Information Management System (LIMS), etc.) were developed to be used to reliably identify and track samples as they are introduced into laboratories. LIS refers to a software system that can be used to receive, process, and store information generated by laboratory processes. LIMS refers to a software or database system that is used to integrate laboratory software and instruments, manage laboratory samples, standards, users, etc., in guiding laboratory samples through laboratories based on a set of defined processes or workflows for quality control in testing these samples. Since LIMS can facilitate simultaneous tracking of thousands of samples, there remains the need for accurate identification of each sample and the media that holds it.

For example, problems arise when it is desired that a sample be processed entirely through the LIMS and that the media that contains the sample has a machine-readable label so that the sample's diagnosis time in the laboratory can be improved and reliably tracked. Certain conventional laboratory printers are capable of adding machine-readable labels to media. Although the use of machine-readable labeling may provide some improvement in sample diagnosis time, it can also introduce a new set of problems for laboratories and may not even be capable of being performed in certain laboratories due to, for example, the high cost of adding machine-readable identifiers and/or the laboratory's inherent limitations (e.g., space limitation). For example, the use of machine-readable labeling may not be employed in most laboratories as the laboratories are being squeezed by lower government budgets and reimbursements and consequently are having to reduce their physical space (that could have been used to hold large printing equipment) in order to allow for more patient capacity. In addition to not having sufficient space for large printers, these laboratories are also becoming averse to high capital costs relating to the existing printer technologies and are looking for ways to reduce costs and be able to pass their operating expenses on to their patients to help improve their bottom line. Further, laboratories are also being driven to reduce their "green" footprint by reducing consumables and the power requirements.

There are additional problems associated with the aforementioned conventional laboratory printers. For example, while printer capital acquisition costs are extremely high, these printers also require dedicated computers (e.g., personal computers (PCs)) as printer operators or operating computers to print media labels). Because the conventional printers are not designed like general computing printers and still employ old connectivity technologies, these printers require a computer be dedicated as an operator or operating computer for the sole purpose of printing on a particular type of media. One example of the old connectivity technologies is the 9-Pin Serial interface which has become obsolete on general computing platforms, but it is still being used with these conventional laboratory printers and is, at least partially, responsible for extremely slow printing outputs. Further, as aforementioned, these conventional printers are limited to printing only a single type of media (e.g., a cassette or a slide, but not both). This limitation further complicates the laboratory space limitation situation as it requires laboratories to have multiple printers along with multiple corresponding dedicated operating computers for printing on multiple media types, such as requiring one printer and its corresponding operating computer for printing on cassettes and another printer and its corresponding operating computer for printing on slides. As the deprecated operating systems and components of the host computers age, the costs of the systems continually escalate.

Current laboratory printing technologies for conventional laboratory printers include ink-jet and ribbon printers. One problem with the laboratory ink-jet printers is that they require using a special ink that is ultraviolet (UV) sensitive that can be cured so that any chemicals used in the sample diagnosis process do not accidently remove the printed label from the media. However, each time a UV light bulb (that is required to cure the special ink) goes out (typically, without a warning), it carries the potential to contaminate hundreds of samples and render them unable to be tracked in the LIMS, by way of the uncured UV sensitive ink. Ribbon printers require that a user correctly and cautiously load a ribbon into a ribbon printer without damaging or wasting too much of the ribbon. Further, instead of pre-loading laboratory media into ribbon printers for automatic printing, a user is required to load the media and continue watching the printer ribbon to be sure that the ribbon does not run to the end and stop all media printing processes.

Conventional printers are high in cost, restricted in their ability to print media (such as limited to printing only one particular type of media), limited in their ways of tracking and identifying samples, wasteful in terms of power and physical footprint and in requiring a dedicated operating computer, employ obsolete connectivity technologies, are error-prone, etc.

BRIEF DESCRIPTION OF THE DRAWINGS

The invention will be understood more fully from the detailed description given below and from the accompanying drawings of various embodiments of the invention. The drawings, however, should not be taken to limit the invention to the specific embodiments, but are for explanation and understanding only.

SUMMARY

Embodiments of the invention that provide a mechanism for remotely facilitating labeling laboratory print media are described. In accordance with the embodiments, there are provided methods, apparatus, and systems for remotely facilitating labeling laboratory print media, such as a method of embodiments of the invention includes placing a user request at a computing system serving as a remote computing system. The user request includes print content to remotely facilitate labeling of a laboratory media within a laboratory environment. The laboratory media may include at least one of a media cassette or a media slide to hold one or more laboratory samples. The method may further include communicating the user request from the computing system to a printing device over a network, the printing device representing a local computing system. The method may further include remotely facilitating the printing device to label the laboratory media.

DETAILED DESCRIPTION

Embodiments of the invention that provide a mechanism for remotely facilitating labeling of laboratory print media are described. A method of embodiments of the invention may include placing a user request at a computing system serving as a remote computing system, with the user request including print content to remotely facilitate labeling of a laboratory media within a laboratory environment. The laboratory media may include at least one of a media cassette or a media slide to hold one or more laboratory samples. The method may further include communicating the user request from the computing system to a printing device over a network, the printing device representing a local computing system. The method may further include remotely facilitating the printing device to label the laboratory media.

Embodiments of the present invention provide for a mechanism for remotely facilitating a print mechanism (e.g., a laser-based printing mechanism having a printer engine) to allow for printing or labeling or imaging of a laboratory print media (e.g., laboratory print media containers, such as cassettes, slides, etc.) that serve as containers for laboratory samples (e.g., histologic specimen, such as microscopic anatomy of cells and tissues of plants, animals, and humans). As the requirements and subsequent costs in healthcare continue to grow, the value and use of laboratory printers continue to increase and drive laboratories and doctors to seek additional or alternative ways to improve their revenue streams and improve profitability. One way of increasing revenue is to reduce cost, such as to print only when necessary and only pay for printing needs as demanded by the workloads necessary (e.g., pay-as-you-go, pay-as-needed, etc.). In one embodiment, a remote print authentication mechanism may receive, process, compile, and communicate the necessary information or data for remotely facilitating printing of laboratory media, allowing the users to take advantage of remote computing devices for customized, low-cost, on-demand, and pay-as-you-go printing of laboratory print media. Since technology and printing needs may vary between various users or software applications, such needs may also vary regarding what information is to be printed, how the information is to be handled, how much information needs be processed and printed, how quickly and efficiently the information may be printed, and the like.

In one embodiment, the print authentication mechanism may be employed on a host printing device or computing system (e.g., server printing/computing system) that employs any number or types of print mechanisms (e.g., laser-based printer, ink-jet printer, ribbon printer, etc.), while a print activation mechanism may be employed on a remote computing system (e.g., remote client computing device, such as a mobile computing device) to access and use the print authentication mechanism on the host printing device to remotely, from the remote computing system, facilitate printing of laboratory print media. In another embodiment, the print authentication mechanism may be employed on a remote computing device, while the print activation mechanism may be employed on the host printing device. In yet another embodiment, the print authentication mechanism and the print activation mechanism may be employed on two separate remote computing systems, while the host printing device may employ one or more print mechanisms that can be accessed and facilitated to print laboratory print media using the print authentication and print activation mechanisms. In yet another embodiment, any combination and number of components and modules of the print authentication and activation mechanisms (as will be described with reference to FIGS. 1, 2A) may be employed on any number and type of computing devices, as desired or necessitated, to allow users to remotely facilitate printing or labeling of laboratory media. Throughout this documents, terms "facilitating remote printing" and "remotely facilitating printing" are used interchangeably and synonymously.

Furthermore, embodiments of the present invention are provided for identifying specimen samples and their media within a laboratory environment by providing a mechanism for remotely facilitating printing of labels or images on multiple types of media (as opposed to printing a single media type that is a common limitation of the conventional media-printing techniques). In one embodiment, the mechanism may also provide laser-based media labeling (or printing or imaging) that is free of ink, ribbons, and various other conventional laboratory and printer consumables; although, as mentioned throughout this document, embodiments of the invention are applicable to and work with any type or number of printing mechanisms, including ink-jet printers, ribbon printers, etc. Further, embodiments of the present invention provide for media labeling that is faster, more efficient, Eco-Green, and more technologically-mature than the conventional media labeling.

In one embodiment, an integrated system having a printer or printing device having a printer engine is provided for labeling laboratory media at the time the samples contained within them are used or introduced to a laboratory. This labeling of the media includes producing an image on the media such that the image includes a relevant human- and machine-readable image having information (e.g., media-related information, sample-related information, user-related information, etc.) that can be used to identify and track various samples contained within the media during the samples' processing within the laboratory environment. For example, if a laser-based print mechanism is chosen by the user, a media image may be produced by remotely facilitating inducing a visible color change on the media using a laser on the laser-sensitive material on the dedicated surface (e.g., a portion of the print media dedicated to imaging) of the media. For example, and in one embodiment, the print engine provides and manages a laser light source, such as a laser, to generate a laser light beam, a moving reflective device (e.g., mirror), and a fixed media surface coated with light-sensitive material. The light beam may be adapted to activate the light-sensitive labeling layer on the media to produce visible change on the media surface from translucent to opaque to form an image on the print media.

Further, for example, a method, apparatus or system may be provided to include a laboratory print media (e.g., medical slide, histology cassette, etc.) labeling mechanism to move a print media coated with a special laser- or light- or photo- or thermal-sensitive material, sealed from external chemical reactions using a chemical-resistance material coating to print a label or image on the print media at a pre-determined print location of a printer using a light source (e.g., a laser) of the printer to temporarily or permanently imprint or display the image or data by activating the laser-sensitive material on the print media. The mechanism may further include moving the print media from the pre-determined print location to the eject location of the printer for human or robotic retrieval. The printer may include a laser focused on the angle of the print media such that the printing remains directly focused to the coating or the dedicated label surface of the print media. Further, the printed data or image or label is entirely encapsulated within the laser-sensitive material and sealed onto the dedicated label surface of the print media so that the image is proof against accidental removal or damage during subsequent handling or treatment of the laboratory media. The media is then transported onto an eject location of the printing device or apparatus. Further, the printing medium contains a laser-sensitive ink that is sealed in an immiscible coating agent.

Figure 1:
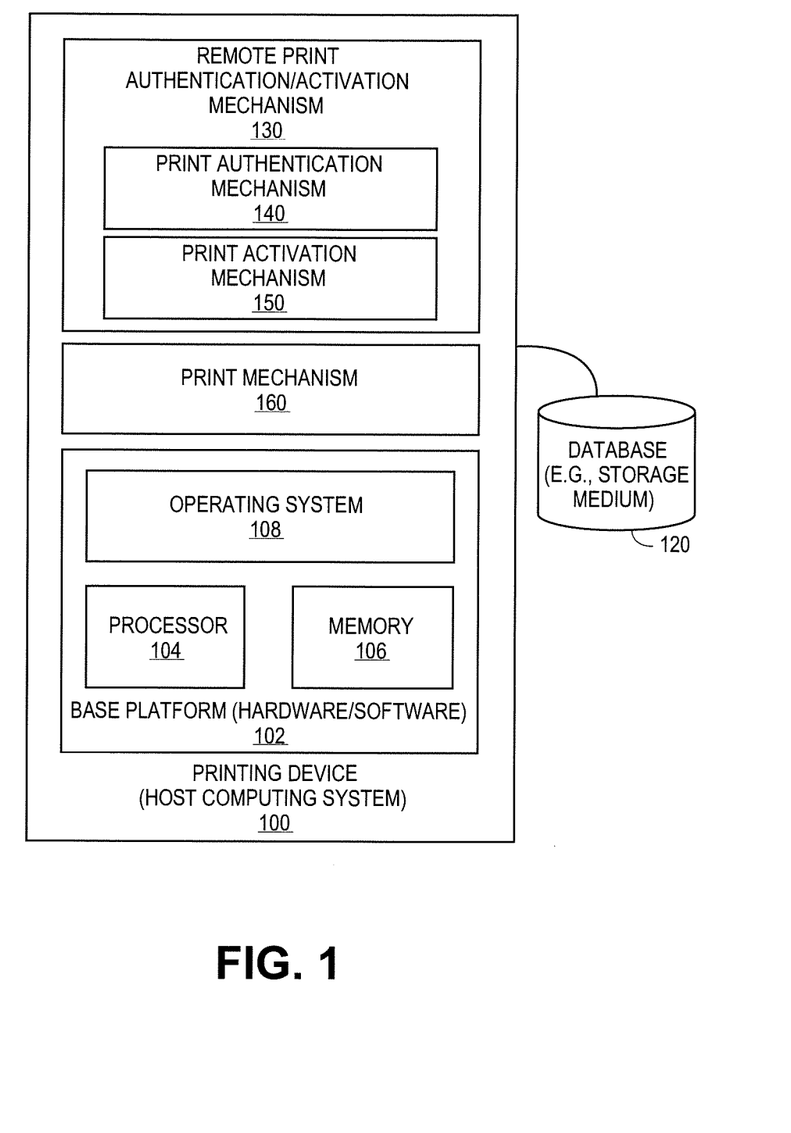
FIG. 1 illustrates a printing device employing a remote print authentication/activation mechanism for remotely facilitating printing of laboratory print media according to one embodiment of the invention.

FIG. 1 illustrates a printing device 100 employing a remote print authentication/activation mechanism 130 for remotely facilitating printing of laboratory print media according to one embodiment of the invention. In one embodiment, the remote print authentication/activation mechanism ("remote print mechanism") 130, employed at the printing device 100, includes a print authentication mechanism ("authentication mechanism") 140 and a print activation mechanism ("activation mechanism") 150 to facilitate a print mechanism 160 (e.g., laser-based print mechanism, ribbon-based print mechanism, ink jet-based print mechanism, etc.) to print laboratory print media (e.g., slides, cassettes, etc.). In one embodiment, as will be further described with reference to FIG. 2B, the authentication mechanism 140 may be employed at the printer 100, while the activation mechanism 150 may be employed at a remote computing device. In another embodiment, the authentication mechanism 140 may be employed at a remote computing device, while the print activation mechanism 150 may be employed on the printing device 100. In yet another embodiment, the authentication mechanism 140 and the print activation mechanism 150 may be employed on two separate and remote computing systems and can be used together to remotely facilitate the print mechanism 160 at the printing device 100 to label a print media. In yet another embodiment, any combination and number of components and modules of the print authentication and activation mechanisms 140, 150 (as will be described with reference to FIG. 2A) may be employed on any number and type of computing devices, as desired or necessitated, to allow users to remotely facilitate labeling of laboratory media.

Printer 100 serves as a host printing device that includes a base computing/printing platform 102 employing hardware and/or software. Throughout the document, terms "printer" and "printing device" are used synonymously and interchangeably. Base platform 102 includes an operating system 108 serving as an interface between any hardware or physical resources of the printer 100 and a user (e.g., an end-user, such as a laboratory technician or assistant, using the printer 100 to label laboratory media). In some embodiments, the base platform 102 may further include a processor 104, memory devices 106, network devices, printer and other drivers, or the like. Memory devices 106 and/or database 120 (e.g., a remote or local storage medium) may be used to store printing system software, printer-specific data files, media-specific data files, sample-specific data files, etc. It is contemplated that the printer 100 may include various computing features or be a computing device or be part of a computing machine. Terms like "machine", "device", "computer" and "computing system" are used interchangeably and synonymously throughout this document. With regard to the embodiments of the present invention, terms like "labeling", "imaging", and "printing" are used interchangeably and synonymously throughout the documents and refer to imaging (e.g., laser-based labeling) of a dedicated surface (e.g., on a dedicated portion of the surface) of the laboratory media, such as a cassette or a slide, that is capable of holding laboratory samples.

Figure 2A:
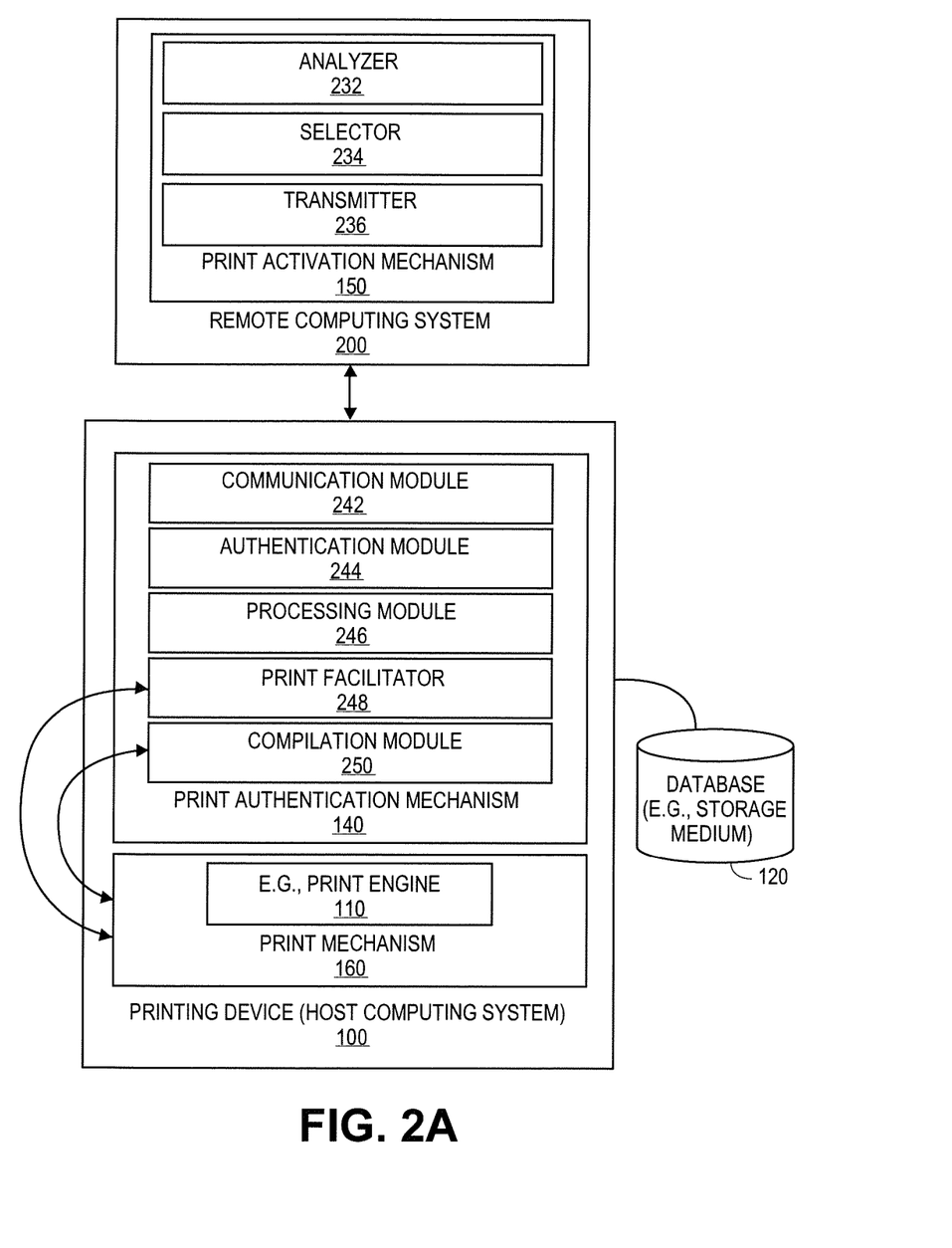
FIG. 2A illustrates a remote print authentication/activation mechanism for remotely facilitating labeling of laboratory print media according to one embodiment of the invention.

FIG. 2A illustrates a remote print authentication/activation mechanism 130 for remotely facilitating labeling of laboratory print media according to one embodiment of the invention. In the illustrated embodiment, the activation mechanism 150 of the print mechanism 130 is employed at a remote computing system (e.g., a mobile computing device), while the authorization mechanism 140 is employed at a host printing or computing device 100. In one embodiment, user (e.g., doctors, hospital staff, laboratory technicians, professors, researchers, etc.) may access and use the activation mechanism 150 on the remote computing system 200 to access and use the authentication mechanism 140 on the printer 100 to remotely choose a print mechanism 160 (e.g., a laser-based print mechanism, as illustrated) from a number and types of print mechanism to facilitate printing of any number and type of media labels on any number and types of laboratory media. Using a combination of the authentication and activation mechanisms 140, 150, a user can remotely perform customized, low-cost and/or pay-as-you-go, printing of print media at the time of user's choosing (e.g., a single or multiple print jobs for immediate printing, future printing, scheduled printing at pre-determined print times or intervals, etc.).

In one embodiment, the authorization and activation mechanisms 140, 150 may be provided as a single new printing software application to be downloaded on a single computing device, as two separate new printing software applications to be downloaded on multiple computing devices 100, 200, as illustrated here, and/or as updates or upgrades to one or more existing printing software applications (e.g., LIS-based software application, etc.), and the like. Further, the remote computing system 200 and the printing device 100 may be in communication over a network (e.g., Internet) and that a user may access the activation mechanism 150 on-line using an user Application Programming Interface ("API" or "interface") provided through the activation mechanism 150. For example, the user may access the activation mechanism 150 using a Web browser (e.g., Chrome®, Explorer®, Safari®, etc.) and/or through a Graphical User Interface (GUI)-based software application employed on the remote computing system 200.

In one embodiment, the authentication mechanism 140 includes, but is not limited to, a communication module 242, an authentication module 244, a processing module 246, a print facilitator 248, and a compilation module 250. Similarly, the activation mechanism 150 contains its own set of components and modules, such as, but not limited to, an analyzer 232, a selector 234, and a transmitter 236. For example, at the remote computing system 200, a user inputs a set of information using the activation mechanism 150, such as via a Web browser or a GUI-based application, to remotely order printing of laboratory print media. This information may include the user's choice of a printer, such as the printer 100, a print mechanism, such as the print mechanism 160, a number and type of print media (e.g., two cassettes, five slides, etc.) to be printed with an image, content (e.g., specimen name, date of extraction, patient name, user name, etc.) of the image to be printed on the print media, a preferred time or schedule of printing (e.g., print the two cassettes now, but print the five slides according to a set printing schedule, such as one each hour, etc.), or the like. Further, the user may select or, in some cases, even propose a cost of printing or simply use the pay-as-you-go option to take advantage of the lowest cost printing option of all the options available to keep within or at least near the printing budget afforded by the user (e.g., doctor, professor, laboratory technician, etc.) or the user's organization (e.g., hospital, university, another laboratory, etc.).

The information provided by the user is then analyzed by the analyzer 232. For example, the analyzer 232 may review the users' printing requests (e.g., preferred printer, time of printing, cost, etc.) and match with any available historical data, e.g., as provided by a storage medium (e.g., database 120 or another database or storage medium in communication with the remote computing system 200), to determine whether the user's requests can be met. If, for example, one or more requests cannot be satisfied (e.g., the user's preferred printer is not available), the analyzer 232 may propose a response with one or more alternatives (e.g., other available printers similar in type or performance to the one requested by the user), if available, to the user so that the user may choose an alternative option. Once the analyzer 232 has analyzed the user information, this analyzed user information is then forwarded on to a selector 234.

The selector 234, in one embodiment, sorts the various user selections (e.g., requested printer, preferred print mechanism, image to be printed, print media on which the image is to be printed, laboratory location, suggested/accepted cost, etc.) into a user request so that it can be properly communicated to the print authentication mechanism 140. In the illustrated embodiment, printer 100 serves as one or more printers of choice of the user. In other words, the user may choose only a single printer 100 or several printers including the printer 100. Further, in the illustrated embodiment, the authentication mechanism 140 is employed on the printer 100, but, as previously mentioned, the authentication mechanism 140 may be employed on any number of printing/computing devices, including the remote computing device 200.

The user request is then transmitted to the authentication mechanism 140, via the transmitter 236 at the activation mechanism 150 and a communication module 242 at the authentication mechanism 140. An authentication module 244 of the authentication mechanism 140 is then used to authenticate and authorize the user request and its aforementioned contents as well as authorize and authenticate some other information that may be contained in or associated with the user request, such as the user profile, the activation mechanism 150 accessed by the user, the remote computing system 200 from where the user request was received, the network (e.g., an Intranet) or server (e.g., Web server) over which the request was received, etc. Once the authentication is performed by the authentication module 244, the user request is forwarded on to a processing module 246. The processing module 246 may perform further analysis (e.g., in addition to the analysis performed by the analyzer 232 at the activation mechanism 150) to re-verify user preferences and requests contained within the user request by, for example, matching the content with any available relevant information (e.g., the current printing costs, historic user requests, user print request pattern, etc.) stored at the database 120.

The processing module 226 then forwards the processed user request on to a print facilitator 248 that communicates with or facilitates the print mechanism 160 to start printing the laboratory print media per the user request. Once the printing is performed, a compilation module 250 then compiles any number of reports (or datasets) based on the user request and its performance. These reports are then stored at the database 120 to be accessed and referenced in the future by, for example, the user, the analyzer 232, the processing module 246, etc. For example, a report may include a list of user requests, a historical perspective of user requests, a history of printing costs paid by the user, etc. As aforementioned, embodiments of the present invention can work with and are applicable to any number and types of print mechanisms; however, in the illustrated embodiment, as an example and for brevity, simplicity and ease of understanding, a laser-based print mechanism 160 having a print engine 110 is used to be shown as preferred by the user.

In one embodiment, the authentication and activation mechanisms 140, 150 may be employed on the same machine, such as the remote computing system 200. Similarly, in another embodiment, the authentication mechanism 140 may be employed on the remote computing system 200, while the activation mechanism 150 may be employed on another computing system, including the printer 100. Depending on the employment of the authentication and activation mechanisms 140, 150 on various computing systems, the distribution and/or employment of their components and modules 232-236, 242-250 may also change, including adding or removing or changing one or more modules 232-236, 242-250, as necessitated or desired. For example, the activation mechanism 150 may include some of the modules 242-250 of the authentication mechanism 140 and vice versa. Further, one or both of the activation and authentication mechanisms 140, 150 be provided as one or more independent or standalone printing software applications and/or as an upgrade or update to one or more existing printing software applications (e.g., LIS-based software application, etc.), or the like, employed on one or more of the printer 100, the remote computing system 200, and/or one or more other computing/printing systems, etc.

In one embodiment, the printer engine 110 is used for identifying laboratory samples (e.g., histology specimen, etc.) and their media containers by providing laser-based labeling of various types of laboratory print media (e.g., cassettes, slides, test tubes, flasks, etc.) that serve as the media containers for the samples. As will be further described with reference to FIG. 2B, in one embodiment, printer engine 110 includes various components and modules of its own, such as, but is not limited to, a communication controller 202, a printer controller 204, a laser controller 206, a laser beam mirror controller 208, a media load and eject controller 210, and light source, such as a laser 212. It is contemplated that the printer engine 110 may include or be in communication with other computing and printing components, such as processors, memory devices, display devices, drivers, graphics cards, and the like, of its own printer 100 or other computing systems 200, to facilitate computing and printing functions and provide the desired capability and connectivity within a laboratory environment.

Figure 2B:
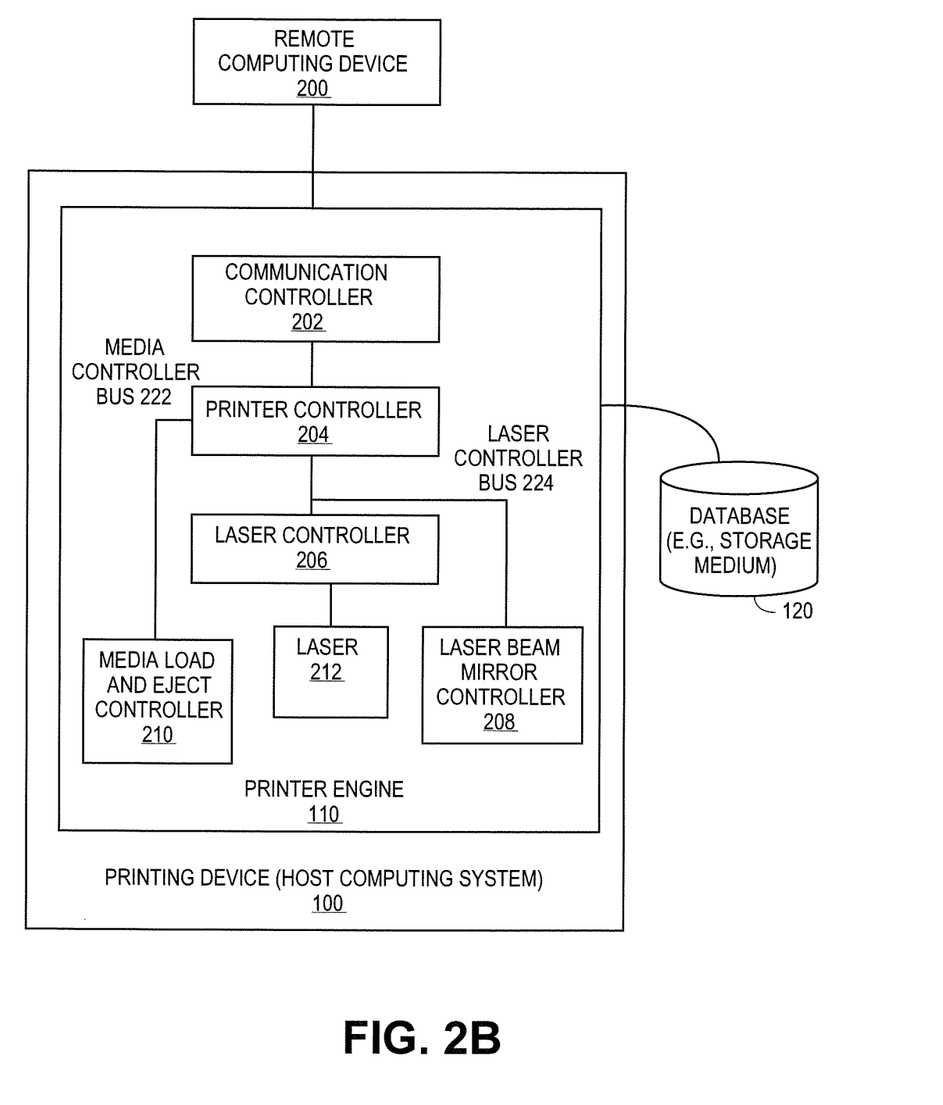
FIG. 2B illustrates a print engine and its print functionalities according to one embodiment of the invention.

Further, the printer engine 110 provides a laser-based imaging of print media that is faster (e.g., prints through parallelization of the printing process), technologically-advanced (e.g., employs laser-based labeling (which is without the use of ink or ribbon) and modern communication and connection capabilities, etc.), more efficient (e.g., low power use, small physical footprint, laser-based printing that stays intact and can be easily tracked throughout laboratory sample processing), relatively inexpensive to purchase, maintain and operate compared to the conventional laboratory printers, and the like.

In one embodiment, the printer engine 110 facilitates producing laser-based images on the surface of any type of print media such that a laser beam is sufficiently articulated across the entire surface of the media to form an image to be printed on a particular portion of the media surface that is referenced as the dedicated labeling surface and used to a label or image. In the illustrated embodiment, the printer engine 110 may be facilitated, using the authentication and activation mechanisms 140, 150, to receive the user request from the remote computing device 200, through, for example, the print facilitator 248, to direct the loading of the user-requested print media, form the requested image on that print media, eject the print media, and communicate any resulting information back to the compilation module 250 to compile a relevant report to be transmitted back to the user via the computing system 200. In one embodiment, a user (e.g., an end-user, such as a laboratory technician) may choose to interact directly with the printer 100 (e.g., using a touch panel of the printer 100). For example, the user may choose a direct interaction with the printer 100 by selecting, for example, a print media option (e.g., label cassette, label slide, etc.) on the touch panel of the printer 100.

Now referring to FIG. 2B, it illustrates the print engine 110 and its print functionalities according to one embodiment of the invention. In one embodiment, the user request is received at the print engine 110 from the print facilitator 248 of the authentication mechanism 140. For example and more specifically, a printer controller 204 of the print engine 110 receives the user request, via a communication controller 202, and then forwards, via a media controller bus 222, the user request to a media load and eject controller 210 to load the relevant print media (e.g., cassette or slide) into the printer's print staging area that serves as a dedicated area (e.g., slot, tube, hopper, flatbed, etc.) of the printer 100 to be used to load, hold, and eject a print media. For example, depending on the user's choice of media, one or more cassettes or slides may be loaded into the print staging area by a human being (e.g., a laboratory technician) or machine, such as a robot. Further, an already-loaded media that is being held in the print staging area may be selected for processing as triggered by the media load and eject controller 210 upon receiving the user request. Any image and/or media ("image/media") information specific to the print media that is being printed may be provided by the user in the user request, retrieved from the database 120, and/or obtained from a storage medium in communication with the remote computing device 200, or the like. The image/media information may include any range of data about the media (e.g., the type of media, etc.) that is being labeled and the image (e.g., project name, sample identification, sample type, etc.) that is being printed on the media as well as relevant information about the user (e.g., user name, user title, etc.) and the laboratory (e.g., laboratory name, location, etc.) that are involved in the processing of samples, and the like.

Printer controller 204 of the print engine 110 may then send the image/media information to a laser controller 206 which then instructs lighting or image device, such as a laser 212 about when to turn on and off as the laser 212 is moved across the media surface by reflecting off of, for example, a laser beam mirror being controlled by the laser beam mirror controller 208. Laser controller 206 may communicate the instructions to the laser via a laser beam mirror controller 208 and further via a laser controller bus 224. Simultaneously, the printer controller 204 may send the image/media information of the user request to instruct the laser beam mirror controller 208 regarding where or which way to move as the laser 212 is pulsed via the laser controller 206 so that an image may be printed or "lased" onto the dedicated media surface of the print media.

Once the laser beam has been moved and pulsed on and off by the laser 212 across the entire surface of the media, the image is determined to be created. Once the image has been created, the printer controller 204 instructs the laser controller 206 to turn off the laser 212. Simultaneously, the printer controller 204 may instruct the laser beam mirror controller 208 to return to its default or home position so that the laser 212 can be reset for the next media that is chosen for labeling and loaded into the print staging area. The printer controller 204 then instructs the media load and eject controller 210 to eject the current, already processed, media from the print staging area of the printer 100.

In one embodiment, a laser beam emitted from the laser 212 may be positioned on the surface of the media using a laser beam positioner that is controlled by the laser beam mirror controller 208 and may be presented, for example, in the form of a micro-electro-mechanical systems (MEMS) mirror. In another embodiment, galvanic actuated mirrors or rotating polygon mirrors may be used to perform the desired functionality. Further, the laser controller 206 may include an array of functionalities of the laser beam or the laser beam mirror positioner which may be controlled by software to emulate the functionality of printing the image on the media.

Furthermore, in one embodiment, various printing instructions may be loaded into the printer controller 204 from a suitable printer communications device connected to an external data source, such as the database 120, via an external communication device interface provided by the communication controller 202. The on-board printer controller 204 controls how these external communications devices, including the remote computing system 200 and the database 120, are accessed via external communication device interfaces provided by the communication controller 202 to pass data from these external sources to the printer controller 204 to control the laser controller 206 and the aforementioned media printing tasks.

Figure 3:
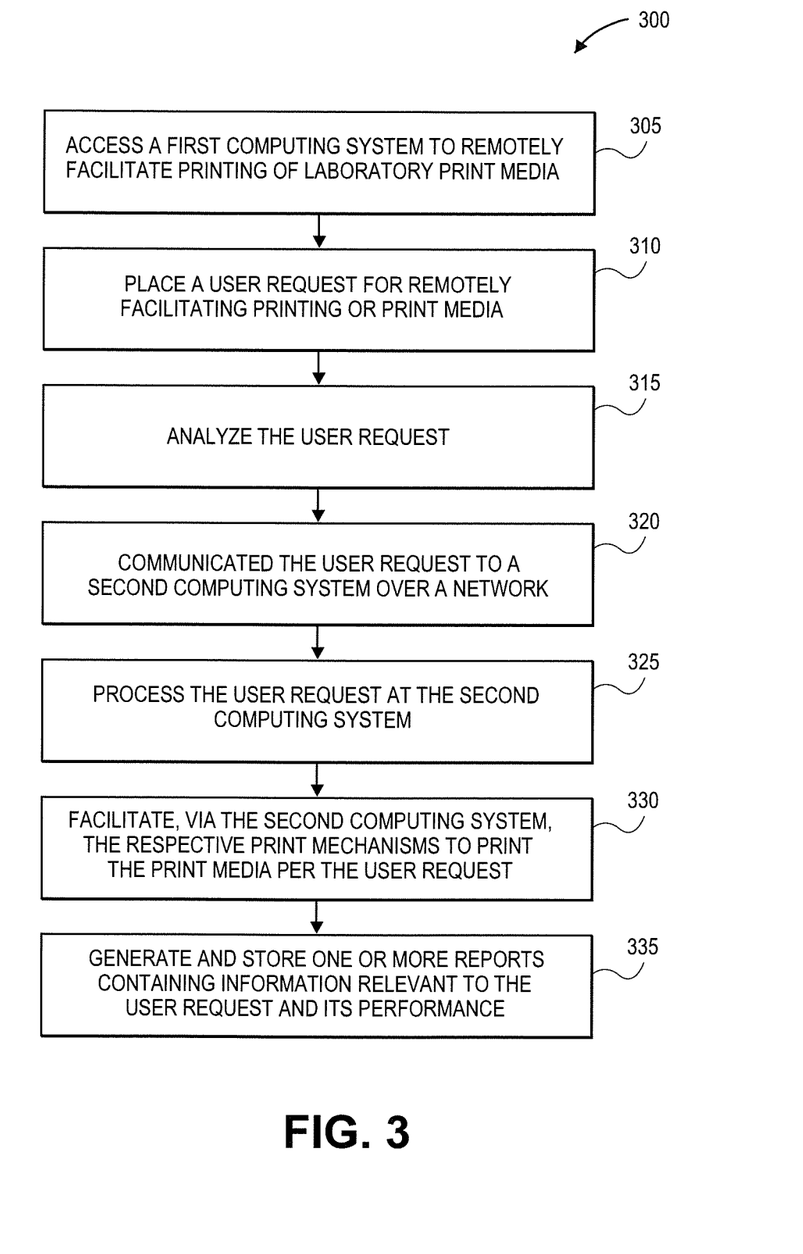
FIG. 3 illustrates a method for remotely facilitating labeling of laboratory print media according to one embodiment of the invention.

FIG. 3 illustrates a method 300 for remotely facilitating labeling of laboratory print media according to one embodiment of the invention. Method 300 may be performed by processing logic that may comprise hardware (e.g., circuitry, dedicated logic, programmable logic, microcode, etc.), software (such as instructions run on a processing device), or a combination thereof, such as firmware or functional circuitry within hardware devices. In one embodiment, method 300 is performed by the remote print authentication/activation mechanism (including print activation and print authentication mechanism) of FIG. 1.

Method 300 begins at block 305 by having a user (e.g., a laboratory technician, a research assistant, a doctor, a professor, etc.) access a first computing system to facilitate remote printing of laboratory print media. The first computing system may include a client computing device (e.g., a mobile computing device) that employs any combination of a print activation mechanism and/or a remote print authentication mechanism. The combination refers to various modules and components of the authentication and activation mechanisms (as described with reference to FIG. 2A) that may be provided or downloaded as part of one or more new or updated printing software applications. At block 310, the user places a user print request for facilitating remote printing. The user request may specify types and number of print media (e.g., cassettes, slides, etc.) that the uses wishes to print using any type and number of printing mechanisms (e.g., laser printing, ink-jet printing, ribbon printing, etc.). The user request may also include other essential information, such as the printing cost the user has authorized (e.g., based on the pay-as-you-go technique), user's preferred method of payment (e.g., credit card, bank account, electronic checks, payment organizations, such as PayPal®, etc.), content of the image(s) to be printed on the print media, timing of printing (e.g., print immediately, print at a specified future time, print periodically, etc.), and the like.

At block 315, the user request is analyzed. The user request analysis include reviewing and analyzing the information contained within the user request, as mentioned above. For example, based on the printing mechanisms specified by the user, the process of analyzing seeks the requested printing mechanisms and may respond back to the user (e.g., the requested printing mechanisms found, one or more of the requested printing mechanisms not found, the requested printing mechanisms found but the cost of printing has gone up or down for one or more of the requested printing mechanisms, etc.). The response back (e.g., an analysis report) may allow the user to alter the user request, as desired or necessitated.

At block 320, the user request is then communicated, over a network, to a second computing system to facilitate printing according to the user request. The second computing system may include one or more computing systems (serving as server/host or intermediary computing systems) in communication with one or more printing devices having the requested print mechanisms. The second computing system may include one or more printing devices employing the requested print mechanisms. Further, like the first computing system, the second computing system(s) may employ any combination of the activation and authentication mechanisms, where, as aforementioned, the combination refers to various modules and components of the authentication and activation mechanisms and may be provided or downloaded as part of one or more new or updated printing software applications.

At block 325, the user request is processed at the second computing system. The processing of the user request may include, for example, a check of all requested printing mechanisms for, for example, availability, cost, etc., a verification of any information the printing mechanisms need to get ready for printing, signaling or requesting of loading of the requested print media into stage areas of the requested printers (where loading of the print media may be performed by a human being or a robot or a device, etc.), and the like. At block 330, the second computing system facilitates the respective print mechanisms to print the print media per the user request. At block 335, one or more reports containing relevant information (e.g., user profile, user print history, print media profiles, printing mechanism profiles, etc.) are generated and then stored at a database for future reference and/or provided to the user via the first computing system.

Figure 4:
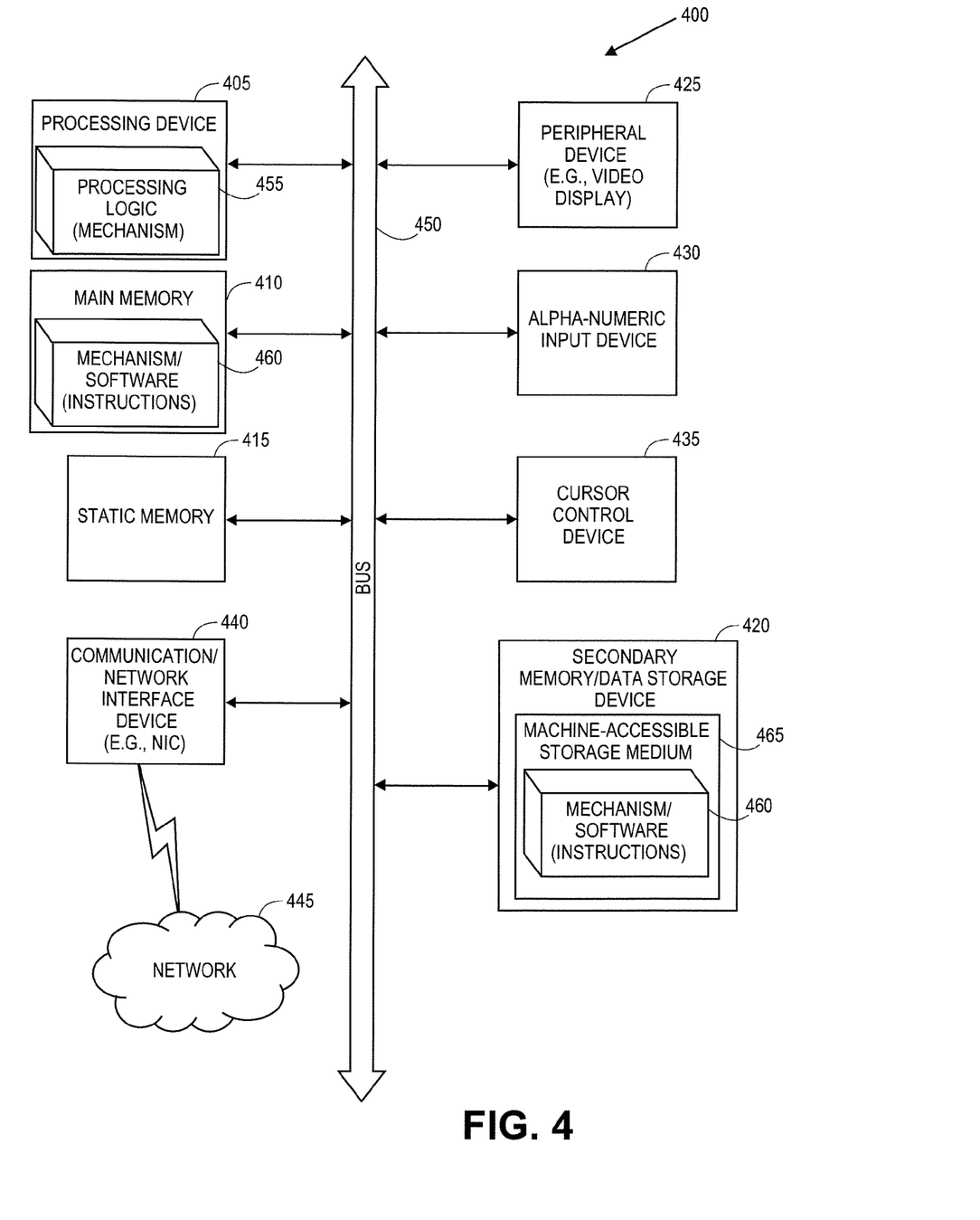
FIG. 4 illustrates a computer system according to one embodiment of the invention.

FIG. 4 illustrates a computer system for employing a printer engine of FIG. 1 according to one embodiment of the invention. Computer system 400 represents or includes a basic circuitry to support remote print authentication/activation mechanism (including print authentication mechanism and print activation mechanism) of FIGS. 1 and 2A and its employer computing device (e.g., printing device and remote computing device of FIG. 2A) providing printing mechanisms (e.g., laser-based printing mechanism having a print engine of FIG. 2A) to facilitate remote printing or remotely facilitating printing of laboratory print media within laboratory environment. In one embodiment, computer system 400 provides the basic circuitry that is employed within the printer to represent the printer as a printing device or, in another embodiment, the computer system 400 may represent an outside-the-printer (local or remote) basic circuitry that is in communication with and facilitates the printer to perform its printing tasks. Computer system 400 may include and function in a server or client computer system capacity in, for example, a server-client environment. Computer system 400 may be the printer of FIG. 1, a personal computer (PC), a Personal Digital Assistant (PDA), a computer pad or tablet, a smart mobile phone, a web server, or any data processing machine capable of storing and executing instructions to perform various tasks (including the ones performed by the remote print mechanism of FIG. 1) mentioned throughout this document.

Although the computer system 400 shown is a single machine, it is contemplated that the term "machine", as referred to in this documents, may include any number of machines in communication with each other or other remote machines. Computer system 400 may be in communication with other machines over a network (e.g., local area network (LAN), wide area network (WAN), metropolitan area network (MAN), intranet, the Internet, etc.) as connected or networked through a communication/network interface device 440 (e.g., network interface card (NIC), USB connection, modem, other devices such as to connect to Ethernet, token ring, etc.). Further, computer system 400 may be accessed by, or communicated with, using various other input/output (I/O) devices, such as an input device, such as an alpha-numeric input device 430 (e.g., keyboard) and/or a cursor control device 435 (e.g., mouse), and a peripheral display device 425 (e.g., a video display device, such as a liquid crystal display (LCD), a cathode ray tube (CRT), etc.) and other similar devices, such as speakers, microphones, etc., connected through a graphics port, chipset, or another human or machine interface device.

Computer system 400 includes a processing device 405. Processing device 405 represents one or more general-purpose processing devices (such as a microprocessor, central processing unit, etc.) and more particularly, the processing device may be complex instruction set computing (CISC) microprocessor, reduced instruction set computer (RISC) microprocessor, very long instruction word (VLIW) microprocessor, or a processing device implementing other instruction sets or a combination of instruction sets. Processing device 405 may also be one or more special-purpose processing devices (e.g., an application specific integrated circuit (ASIC), a field programmable gate array (FPGA), a digital signal processor (DSP), a microprocessor, a network processor, etc.). In one embodiment, processing device 405 is configured to execute the processing logic 455 (e.g., remote print authentication/activation mechanism processing logic) for performing the operations and methods discussed herein and as performed by the remote print authentication/activation mechanism of FIG. 1.

Computer system 400 further includes a main memory 410 (e.g., read-only memory (ROM), flash memory, random access memory (RAM), dynamic RAM (DRAM), synchronous DRAM (SDRAM), etc.), a static memory 415 (e.g., flash memory, static random access memory (SRAM), etc.), and other storage devices 420 (e.g., a data storage device or a magnetic disk or optical disc in the form of a drive unit, which may include fixed or removable machine-accessible or computer-readable storage medium), which communicate with each other via a bus 450. Storage 420 may include a non-transitory machine-accessible storage medium 465 that may then be used to store one or more sets of instructions 460 (e.g., remote print mechanism instructions). These instructions 460 may be transmitted or received over a network via the network interface device 440 coupled with a network 445 (e.g., Internet). The instructions 460 of the authentication and activation mechanisms of FIG. 2A may also reside, completely or at least partially, within the main memory 410 and/or within the processing device 405 as processing logic 455 (e.g., remote print mechanism processing logic) during execution thereof by the computer system 400, the main memory 410 and the processing device 405 also constituting a non-transitory machine-readable storage media. Further, in one embodiment, the authentication and activation mechanisms of FIG. 2A may be employed (entirely) on a single machine, such as computer system 400, or (partially or entirely) on different computer systems.

While the non-transitory machine-accessible storage medium 465 is described as a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instruction for execution by the machine and that cause the machine to perform any one or more of the methodologies of the present invention. The term "machine-accessible storage medium" shall accordingly be taken to include, but not be limited to, solid-state memories, and optical and magnetic media.

As aforementioned, in one embodiment, the printer engine is represented as and includes modules, components and other features, as described throughout this document, can be implemented as discrete hardware components or integrated in the functionality of hardware components such as Application-Specific Integrated Circuit (ASIC), Field-Programmable Gate Array (FPGA), Digital Signal Processor (DSP), etc., or as software or as firmware or functional circuitry.

Throughout the foregoing description, for the purposes of explanation, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions above are presented in terms of algorithms and symbolic representations of operations on data bits within a computer memory. An algorithm is here, and generally, conceived to be a self-consistent sequence of processes or steps leading to a desired result, and these processes or steps are those requiring physical manipulations of physical quantities manifesting as electrical or magnetic signals (e.g., bits, values, elements, symbols, characters, terms, numbers, etc.) capable of being stored, transferred, combined, compared, and otherwise manipulated. Further, certain terms (such as "accessing", "placing", "analyzing", "communicating", "processing", "compiling", "saving", "storing", "generating", "receiving", "forwarding", "printing", "labeling", "imaging", "directing", "instructing", "displaying", "detecting", etc.) may be associated with various physical quantities and refer to action or processes or steps of processing logic of a processing device, such as the processing device 405, of a data processing device, such as the computer system 400.

It is contemplated that apparatus may be specially constructed for the required purposes, or it may comprise a general purpose computer selectively activated or reconfigured by a computer program stored in the computer. Such a computer program may be stored in a non-transitory machine readable storage medium, such as, but not limited to, any type of disk including floppy disks, optical disks, magnetic-optical disks, ROMs, compact disk ROMs (CD-ROMs), RAMs, erasable programmable ROMs (EPROMs), electrically EPROMs (EEPROMs), magnetic or optical cards, or any type of media suitable for storing electronic instructions, each coupled to a computer system bus. However, it is further contemplated that methods (e.g., algorithms, processes, steps, etc.) and displays presented herein are not inherently related to any particular computer system or apparatus. Various general purpose systems may be used with programs in accordance with the teachings herein, or it may prove convenient to construct more specialized apparatus to perform the required method steps. Moreover, the present invention is not described with reference to any particular programming language or operating system or software platform. For example, it is appreciated that a variety of programming languages may be used to implement the teachings of the invention as described herein.

As aforementioned, embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., computer system 400). For example, a non-transitory machine-readable 465 (e.g., a non-transitory computer-readable) medium includes a machine (e.g., a computer) readable storage medium (e.g., ROM, RAM, magnetic disk storage media, optical storage media, flash memory devices, etc.), a machine (e.g., computer) readable transmission medium (non-propagating electrical, optical, or acoustical signals), etc.

Many of the methods are described in their most basic form, but processes can be added to or deleted from any of the methods and information can be added or subtracted from any of the described messages without departing from the basic scope of the present invention. It will be apparent to those skilled in the art that many further modifications and adaptations can be made. The particular embodiments are not provided to limit the invention but to illustrate it. The scope of the embodiments of the present invention is not to be determined by the specific examples provided above but only by the claims below.

If it is said that an element "X" is coupled to or with element "Y," element X may be directly coupled to element Y or be indirectly coupled through, for example, element "Z". When the specification or claims state that a component, feature, structure, process, or characteristic X "causes" a component, feature, structure, process, or characteristic Y, it means that "X" is at least a partial cause of "Y" but that there may also be at least one other component, feature, structure, process, or characteristic that assists in causing "Y." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements. Further, an embodiment is an implementation or example of the present invention. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments.

Any of the above embodiments may be used alone or together with one another in any combination. One or more implementations encompassed within this specification may also include embodiments that are only partially mentioned or alluded to or are not mentioned or alluded to at all in this brief summary or in the abstract. Although various embodiments may have been motivated by various deficiencies with the prior art, which may be discussed or alluded to in one or more places in the specification, the embodiments do not necessarily address any of these deficiencies. In other words, different embodiments may address different deficiencies that may be discussed in the specification. Some embodiments may only partially address some deficiencies or just one deficiency that may be discussed in the specification, and some embodiments may not address any of these deficiencies.

In the foregoing specification, the invention has been described with reference to specific exemplary embodiments thereof. It will, however, be evident that various modifications and changes may be made thereto without departing from the broader spirit and scope of the invention as set forth in the appended claims. The Specification and drawings are, accordingly, to be regarded in an illustrative rather than a restrictive sense.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the invention.

What is claimed is:

1. A method comprising:
   receiving a print request at a computing system, the print request including a request to print an image on a dedicated portion of a laboratory print media container holding one or more specimens, wherein types of the print media container include one or more of a cassette, a slide, a test tube, and a flask, wherein the computing device includes a printing device;
   analyzing contents of the print request, wherein the contents include user preferences specifying one or more of a type of the laboratory print media container to be printed, a type of a print technique to be used for printing of the image, an authorized printing cost to be received from a user, a preferred method for payment of the authorized printing cost, a subject matter to be included in the image, and a time at which to print the image; and
   facilitating, locally or remotely, the printing device to print the image on the dedicated portion of the print media container based on the print format and in accordance with the user preferences as determined from analysis of the contents of the print request, wherein the image is printed by inducing a visible color change from translucent to opaque on the dedicated portion,
   wherein the dedicated portion is coated with photo-sensitive material having chemical-resistance material that is activated to seal the dedicated portion for protecting the printed image from external chemical reactions, wherein the printed image is entirely encapsulated within the photo-sensitive material and sealed onto the dedicated portion such that the printed image remains proof against one or more of accidental removal and handling error or mistreatment.

2. The method of claim 1, wherein the print request further comprises a request to print a label including a textual message, wherein the image includes a picture or an animated message, wherein the print request is received from a second computing device coupled, locally or remotely, to the computing device, wherein remotely facilitating comprises remotely directing the printing device to perform printing of the image on the dedicated portion of the laboratory print media container, wherein the photo-sensitive material includes at least one of laser-sensitive material, light-sensitive material, and thermal-sensitive material.

3. The method of claim 1, wherein the printing of the image is performed using a laser-based print mechanism to direct, in response to the print request, a light source to label the laboratory print media container by generating the image on the dedicated portion of a surface of the laboratory print media container, wherein the light source includes a laser, wherein directing the light source includes facilitating the light source to generate the image by pulsing on and moving across the dedicated portion by reflecting off of a laser beam mirror.

4. The computer-implemented method of claim 1, further comprising selecting the laboratory print media container based on the user preferences or as determined by an ongoing laboratory workflow process.

5. The computer-implemented method of claim 1, wherein the laboratory print media container is automatically loaded into or ejected from a print staging area of the printing device, wherein the automatic loading or ejection is performed by a mechanical device including a robot.

6. A system comprising:
   a computing device comprising a storage medium having stored thereon instructions, and a processing device to execute the instructions to facilitate a mechanism to perform one or more operations comprising:

receiving a print request at a computing system, the print request including a request to print an image on a dedicated portion of a laboratory print media container holding one or more specimens, wherein types of the print media container include one or more of a cassette, a slide, a test tube, and a flask, wherein the computing device includes a printing device;

analyzing contents of the print request, wherein the contents include user preferences specifying one or more of a type of the laboratory print media container to be printed, a type of a print technique to be used for printing of the image, an authorized printing cost to be received from a user, a preferred method for payment of the authorized printing cost, a subject matter to be included in the image, and a time at which to print the image; and facilitating, locally or remotely, the printing device to print the label image on the dedicated portion of the print media container based on the print format and in accordance with the user preferences as determined from analysis of the contents of the print request, wherein the image is printed by inducing a visible color change from translucent to opaque on the dedicated portion, wherein the dedicated portion is coated with photo-sensitive material having chemical-resistance material that is activated to seal the dedicated portion for protecting the printed image from external chemical reactions, wherein the printed image is entirely encapsulated within the photo-sensitive material and sealed onto the dedicated portion such that the printed image remains proof against one or more of accidental removal and handling error or mistreatment.

7. The system of claim 6, wherein the print request further comprises a request to print a label including a textual message, wherein the image includes a picture or an animated message, wherein the print request is received from a second computing device coupled, locally or remotely, to the computing device, wherein remotely facilitating comprises remotely directing the printing device to perform printing of the image on the dedicated portion of the laboratory print media container, wherein the photo-sensitive material includes at least one of laser-sensitive material, light-sensitive material, and thermal-sensitive material.

8. The system of claim 6, wherein the printing of the image is performed using a laser-based print mechanism to direct, in response to the print request, a light source to label the laboratory print media container by generating the image on the dedicated portion of a surface of the laboratory print media container, wherein the light source includes a laser, wherein directing the light source includes facilitating the light source to generate the image by pulsing on and moving across the dedicated portion by reflecting off of a laser beam mirror.

9. The system of claim 6, wherein the one or more operations further comprise selecting the laboratory print media container based on the user preferences or as determined by an ongoing laboratory workflow process.

10. The system of claim 6, wherein the laboratory print media container is automatically loaded into or ejected from a print staging area of the printing device, wherein the automatic loading or ejection is performed by a mechanical device including a robot.

11. A non-transitory machine-readable medium having stored thereon instructions which when executed by a machine cause the machine to perform one or more operations comprising:

receiving a print request at a computing system, the print request including a request to print an image on a dedicated portion of a laboratory print media container holding one or more specimens, wherein types of the print media container include one or more of a cassette, a slide, a test tube, and a flask, wherein the computing device includes a printing device;

analyzing contents of the print request, wherein the contents include user preferences specifying one or more of a type of the laboratory print media container to be printed, a type of a print technique to be used for printing of the image, an authorized printing cost to be received from a user, a preferred method for payment of the authorized printing cost, a subject matter to be included in the image, and a time at which to print the image; and facilitating, locally or remotely, the printing device to print the label on the dedicated portion of the print media container based on the print format and in accordance with the user preferences as determined from analysis of the contents of the print request, wherein the image is printed by inducing a visible color change from translucent to opaque on the dedicated portion, wherein the dedicated portion is coated with photo-sensitive material having chemical-resistance material that is activated to seal the dedicated portion for protecting the printed image from external chemical reactions, wherein the printed image is entirely encapsulated within the photo-sensitive material and sealed onto the dedicated portion such that the printed image remains proof against one or more of accidental removal and handling error or mistreatment.

12. The non-transitory machine-readable medium of claim 11, wherein the print request further comprises a request to print a label including a textual message, wherein the image includes a picture or an animated message, wherein the print request is received from a second computing device coupled, locally or remotely, to the computing device, wherein remotely facilitating comprises remotely directing the printing device to perform printing of the image on the dedicated portion of the laboratory print media container, wherein the photo-sensitive material includes at least one of laser-sensitive material, light-sensitive material, and thermal-sensitive material.

13. The non-transitory machine-readable medium of claim 11, wherein the printing of the image is performed using a laser-based print mechanism to direct, in response to the print request, a light source to label the laboratory print media container by generating the image on the dedicated portion of a surface of the laboratory print media container, wherein the light source includes a laser, wherein directing the light source includes facilitating the light source to generate the image by pulsing on and moving across the dedicated portion by reflecting off of a laser beam mirror.

14. The non-transitory machine-readable medium of claim 11, wherein the one or more operations further comprise selecting the laboratory print media container based on the user preferences or as determined by an ongoing laboratory workflow process.

15. The non-transitory machine-readable medium of claim 11, wherein the laboratory print media container is automatically loaded into or ejected from a print staging area of the printing device, wherein the automatic loading or ejection is performed by a mechanical device including a robot.

* * * * *